United States Patent [19]
Belk et al.

[11] Patent Number: 6,064,429
[45] Date of Patent: *May 16, 2000

[54] FOREIGN OBJECT VIDEO DETECTION AND ALERT SYSTEM AND METHOD

[75] Inventors: John Huntley Belk; Michael Tony Gaston, both of St. Louis, Mo.

[73] Assignee: McDonnell Douglas Corporation, St. Louis, Mo.

[*] Notice: This patent issued on a continued prosecution application filed under 37 CFR 1.53(d), and is subject to the twenty year patent term provisions of 35 U.S.C. 154(a)(2).

[21] Appl. No.: 08/912,375

[22] Filed: Aug. 18, 1997

[51] Int. Cl.$^7$ ...................................................... H04N 7/18
[52] U.S. Cl. ........................... 348/128; 348/129; 382/141
[58] Field of Search ..................... 340/500, 506, 340/507, 518; 348/88, 128, 129, 340, 93, 89, 92, 125, 130, 131; 358/313, 314, 107; 250/559.06; 382/1, 110, 112, 141, 162; 209/580; H04N 7/18

[56] References Cited

U.S. PATENT DOCUMENTS

| | | |
|---|---|---|
| 3,243,509 | 3/1966 | Stut . |
| 4,064,534 | 12/1977 | Chen et al. . |
| 4,120,402 | 10/1978 | Swanson . |
| 4,135,204 | 1/1979 | Davis, Jr. et al. . |
| 4,445,185 | 4/1984 | Davis, Jr. et al. . |
| 4,760,444 | 7/1988 | Nielson, et al. . |
| 5,007,096 | 4/1991 | Yoshida ........................................ 382/8 |
| 5,016,099 | 5/1991 | Bongardt et al. ......................... 358/106 |
| 5,058,174 | 10/1991 | Carroll ........................................ 382/1 |
| 5,187,573 | 2/1993 | Yoshida ................................... 358/106 |
| 5,237,407 | 8/1993 | Grezee et al. ........................... 358/107 |
| 5,253,302 | 10/1993 | Massen ...................................... 382/1 |
| 5,263,094 | 11/1993 | Laitinen ..................................... 382/8 |
| 5,333,208 | 7/1994 | Massen ..................................... 348/88 |
| 5,440,650 | 8/1995 | Heida et al. ............................. 382/112 |
| 5,452,370 | 9/1995 | Nagata ...................................... 348/88 |
| 5,495,429 | 2/1996 | Craven et al. ........................... 382/162 |
| 5,533,628 | 7/1996 | Tao ........................................... 209/580 |
| 5,646,682 | 7/1997 | Sogabe .................................... 348/135 |
| 5,652,432 | 7/1997 | Yaginuma ........................... 250/559.06 |
| 5,732,147 | 3/1998 | Tao ........................................... 382/110 |

Primary Examiner—Howard Britton
Assistant Examiner—Tung Vo
Attorney, Agent, or Firm—Alston & Bird LLP

[57] ABSTRACT

A foreign object video detection system comprises a television camera for producing a digital color image of a work surface, a converter having direct memory access to a computer, color detection and color image processing software, logic for discriminating objects deemed to be a foreign object on the work surface or upon a layer of material on the work surface, logic for providing appropriate warning to the operator, and input controls for selecting the area of interest for detection and for optimizing the detection technique based upon the manufacturing situation.

22 Claims, 8 Drawing Sheets

FOREIGN OBJECT VIDEO DETECTION AND ALERT SYSTEM AND METHOD

FIELD OF THE INVENTION

The present invention relates generally to methods and apparatus for video detection of foreign objects on a work surface and warning the operator by computer display representation, warning light, vibrating beeper, and/or audio warning during manufacture of composite structures containing stacked layers of material.

BACKGROUND OF THE INVENTION

In the aerospace industry, composite structures are often chosen instead of metallic structures when high strength to weight ratio is desired, especially for complex shapes. Strength in such composite structures is greatly reduced, however, when defects occur, such as delaminations. The introduction of a foreign object within a stack of composite plies comprising a composite structure can cause such strength-reducing delaminations. In a safety critical application, such as the composite skin of a tactical aircraft wing, such a reduction in strength may exceed allowances, forcing expensive repair or scrapping of the composite structure.

Traditionally, manufacture of such composite structures has often not been automated due to the difficult techniques employed and small numbers produced. Each layer of material, or ply, is placed by hand. Thus, each composite structure may be in a partial state of assembly for an extended period of time with many opportunities for human error in overlooking objects left within the composite plies. After the structure is completely assembled and cured, nondestructive testing may be used to verify fabrication. See FIG. 9.

Although post-manufacturing nondestructive testing may be sufficient for preventing unsafe structures from being used, the cost of repair or replacement is significant if an embedded object is detected. An even more problematic result is when a strength critical structure is flawed by a foreign object that is not detected by post-manufacture testing, leading to catastrophic failure.

Although not utilized during composite structure fabrication, it is known in other industries to employ closed circuit television for process control where the parameter of interest is an edge or boundary which may be compared with a pre-existing reference. For example, U.S. Pat. No. 3,243,509 to Hans Sut discloses a system which employs a TV camera to detect the phase boundary between the solid and liquid phases of a semiconductor rod in a zone melting process. In U.S. Pat. No. 4,064,534 to Tung Chang Chen et al., a TV camera is employed as part of a quality control system in the manufacture of glass bottles with the outline of the finished bottles being compared with that of a reference bottle. In U.S. Pat. No. 4,135,204 to Ray E. Davis, Jr. et al., a TV camera is used to control the growth of a thermometer end opening blister in a heated hollow glass rod by monitoring and iteratively controlling the growth of the edges of the blister using edge detection techniques. In U.S. Pat. No. 4,760,444 to Paul Nielsen et al., the inspected area had to remain in a very specific location so that a scanned image could be directly compared with the known light levels of the inspected area in the desired state.

It is also known to employ a closed circuit television camera in a process for performing pattern recognition and area measurement applications. In U.S. Pat. No. 4,445,185 to Ray E. Davis, Jr., et al., the digital video image is processed in a DRAM of a computer by comparing the subject image with a stored master image in order to determine if a threshold difference is reached. The subject images are thus inspected for flaws by determining whether they exceed this threshold. In U.S. Pat. No. 5,187,573 to Hajime Yoshida, a transparent or translucent article is back lit and the resulting image is subjected to a pattern recognition technique for expected flaws. U.S. Pat. No. 5,452,370 to Yasuyuki Nagata is an example of robotic vision measuring of articles and performing calculations relating to the object prior to manipulation. It is also known to use color in detecting foreign objects. In U.S. Pat. No. 4,120,402 to Ronald Swanson, defective tomatoes or foreign objects are detected by physically placing the object in the correct place for inspection and detecting specific colors for discriminating culls or agricultural debris.

These prior art systems are directed to situations in which manufacturing is automated and the desired state is known. These systems cannot adapt to changes in the process being employed by the operator or adequately interface with the operator. As such, conventional closed circuit televisions have not been capable of effectively monitoring composite structure fabrication.

SUMMARY OF THE INVENTION

It is therefore an object of the present invention to provide video detection of foreign objects and give warning to an operator.

It is another object of the present invention that such warning to the operator include an audio warning, a warning light, beeper vibration, and/or a display of the work surface with each detected foreign object (FO) highlighted.

It is an additional object of the present invention to include several color image processing alternatives for discrimination a foreign object while reducing false alarms. These alternatives include detecting known unacceptable colors, detecting colors on a preparation table not known as acceptable, and detecting a color not present in a prior image.

It is yet another object of the present invention to provide video detection of foreign objects having at least one video camera oriented toward a work surface. The number, position, mobility, and resolution capability of these cameras being selected based upon the size and contour of work surface and size of foreign objects of concern.

It is a further object of this present invention to provide a method for video detection of foreign objects and warning to operators as part of the manufacture of composite structures.

These and other objects are provided, according to the present invention, by processing the video color image of a work surface within a defined area of interest, detecting specific colors associated with foreign objects or colors that differ from the corresponding colors of a prior image of the work surface. If a foreign object is detected, the operator is then warned by highlighting the location of the foreign object upon a computer display and/or by actuating a warning light, audio warning or electromagnetic signal to gain the attention of the operator.

By detecting foreign objects based on the color of the foreign objects, the detection method and apparatus can detect foreign objects that may be of unpredictable shape, color or location. In this regard, the present invention uses the discriminating potential of the different colors of potential foreign objects to optimize the detection algorithms. Advantageously, the apparatus of the present invention does not require the work piece or the camera to be physically moved in order to define the area for comparison. Even if used in its most basic fashion of looking only for foreign objects of predetermined colors, the present invention incorporates a sophisticated operator interface for more flexibly monitoring the process and for providing options for warning the operator.

DETAILED DESCRIPTION OF THE INVENTION

The present invention now will be described more fully hereinafter with reference to the accompanying drawings, in which a preferred embodiment of the invention is shown. This invention may, however, be embodied in many different forms and should not be construed as limited to the embodiments set forth herein; rather, this embodiment is provided so that this disclosure will be thorough and complete, and will fully convey the scope of the invention to those skilled in the art. Like numbers refer to like elements throughout.

Material inadvertently introduced into a product or process is described as a foreign object, or FO. Often in the aerospace industry, it may also be termed foreign object damage, or FOD, emphasizing its result.

Figure 1:
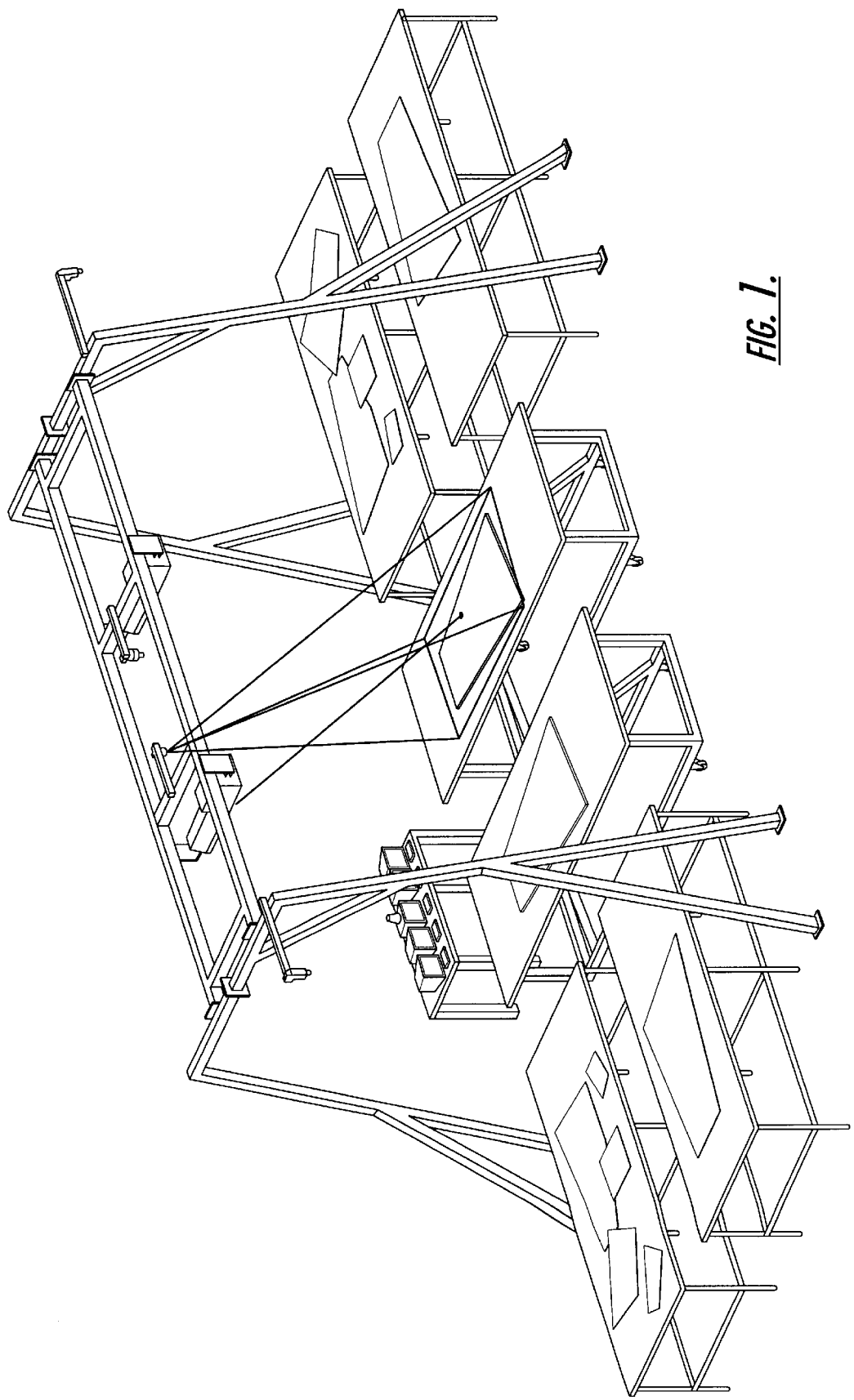
FIG. 1 is an example of incorporating the foreign object video detection method and apparatus of the present invention into an existing apparatus for manufacturing composite structures.

Although the video detection and alert system and method can be implemented in a variety of manners, the video detection and alert system and method of the present invention can be advantageously integrated into an existing manufacturing process with video cameras overlooking the work surfaces as shown in FIG. 1.

Figure 2:
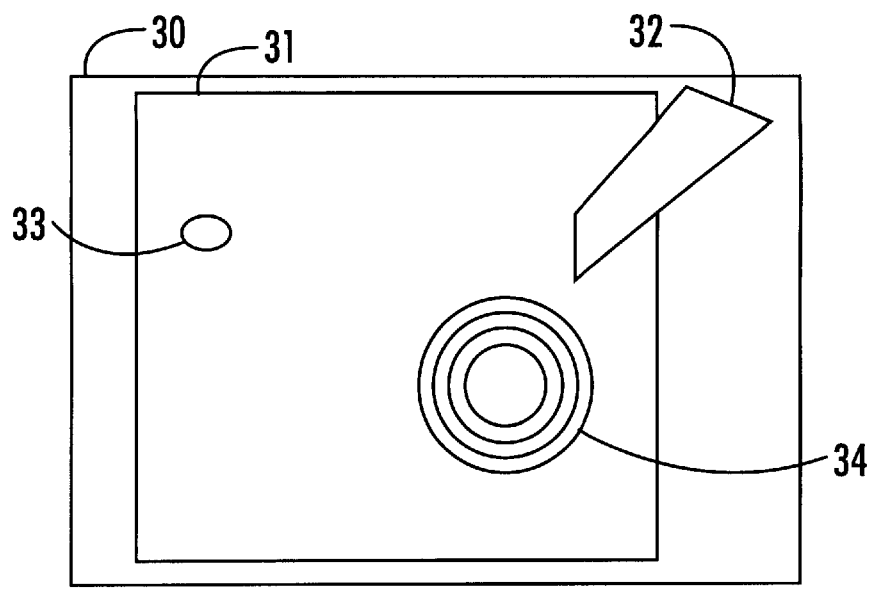
FIG. 2 is color image 1 of 4 of an illustrative display generated by the color image processing system showing a lay-up table before adding a layer of material or a foreign object.
Figure 6A:
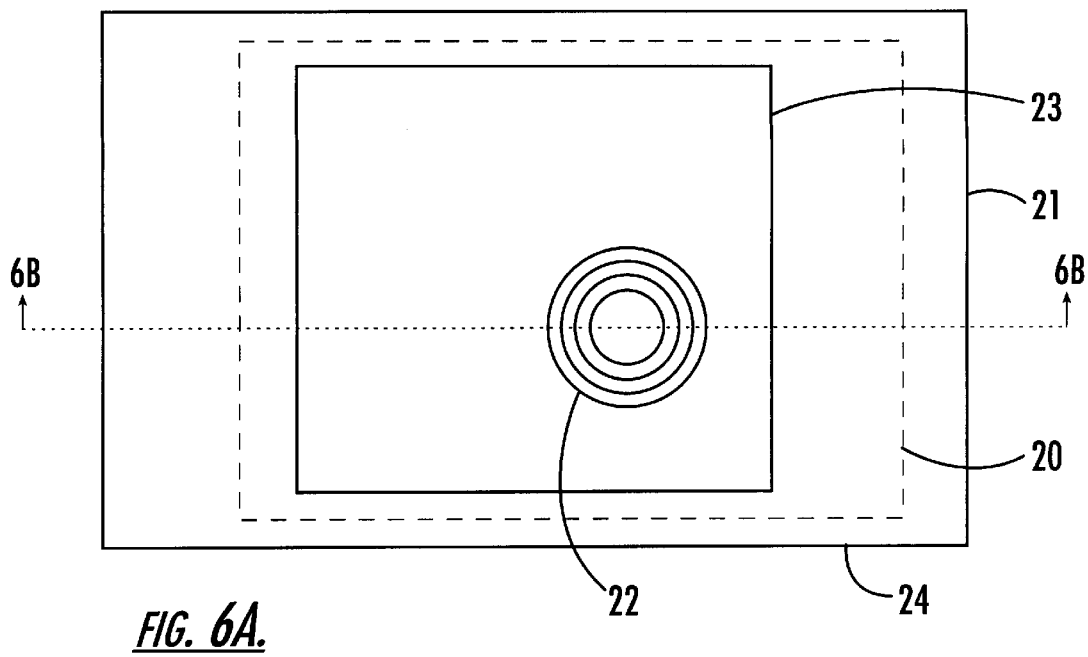
FIGS. 6A and 6B are top and side views of a lay-up table.
Figure 6B:
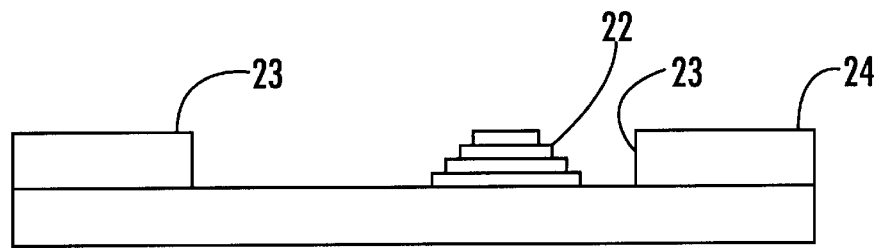
Figure 7:
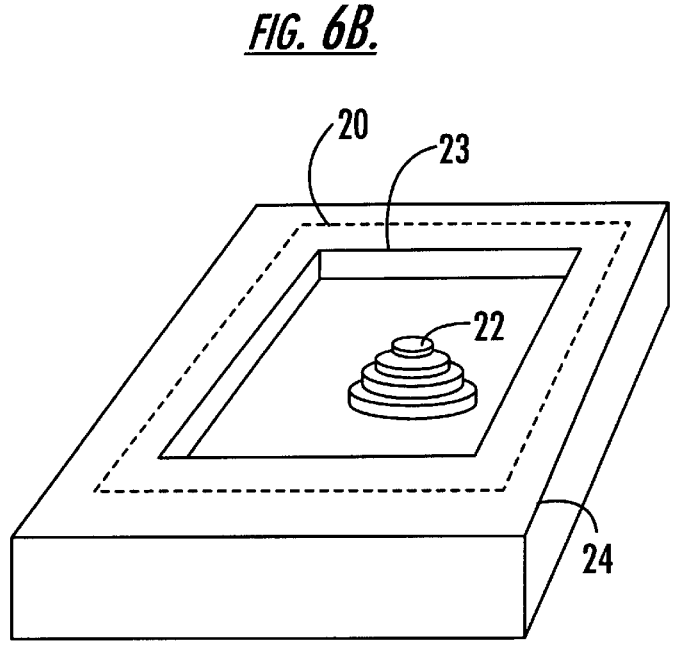
FIG. 7 is a perspective view of the lay-up table.

The inventive nature of the detection portion of the system, as opposed to the warning portion, is best illustrated by a simplified depiction of the processed images. As illustrated in FIG. 6 and FIG. 7, the work surface 24 may have an outermost guide 23 and cutout guide 22 for correctly positioning the layers of material, or composite plies. The video detection and alert system includes a camera having a field of view 20 which does not necessarily need to be coextensive with the space defined by the outermost guide 23 in which the layers of material will be placed. The camera generates video images, such as the video digital image shown in FIG. 2 of the table prior to placement of material or a foreign object. The video digital image 30 corresponds to the field of view 20 of the video camera, and includes an area of interest 31, preferably corresponding to the shape defined by the outermost guide 23. As described below, the area of interest is typically defined by operator input. Although not shown in FIG. 2, the video digital image could include color or contrast changes, such as glare 32 from the illuminating light source or color differences between the cutout guide 22 and the work surface 30 and a nonhomogeneous portion 33 of the work surface 30.

Figure 3:
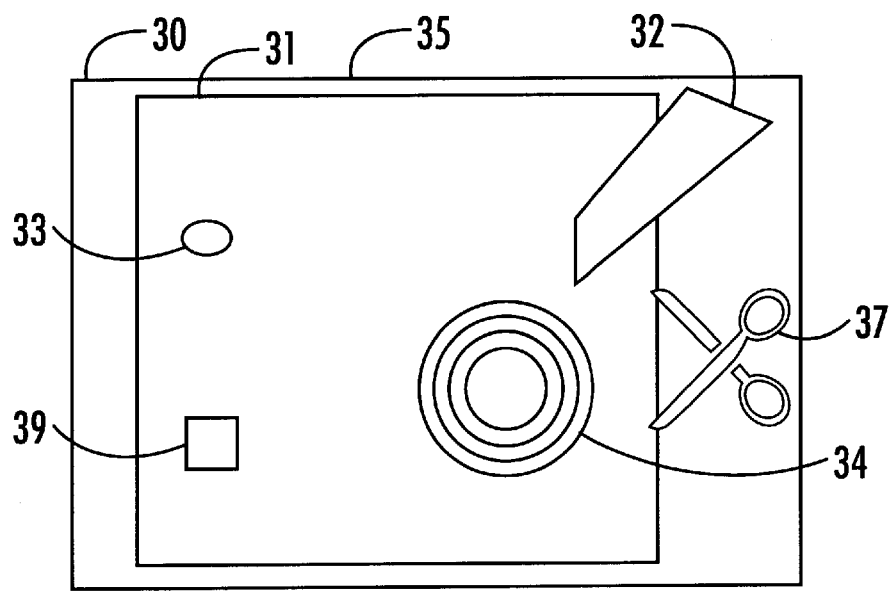
FIG. 3 is color image 2 of 4 of an illustrative display generated by the color image processing system showing a lay-up table after the introduction of a layer of material and foreign objects.
Figure 4:
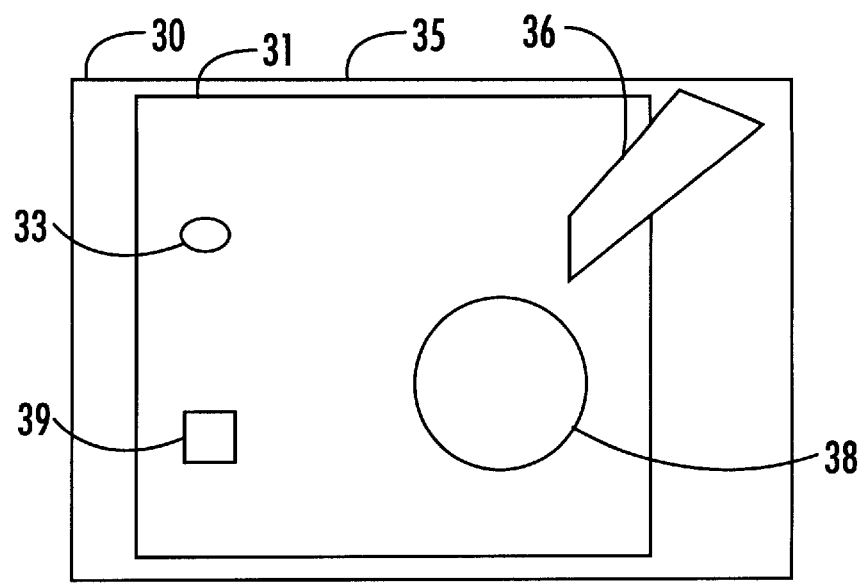
FIG. 4 is color image 3 of 4 of an illustrative display generated by the color image processing system showing a lay-up table after the color image processing system subtracts areas not of concern for foreign objects.
Figure 5:
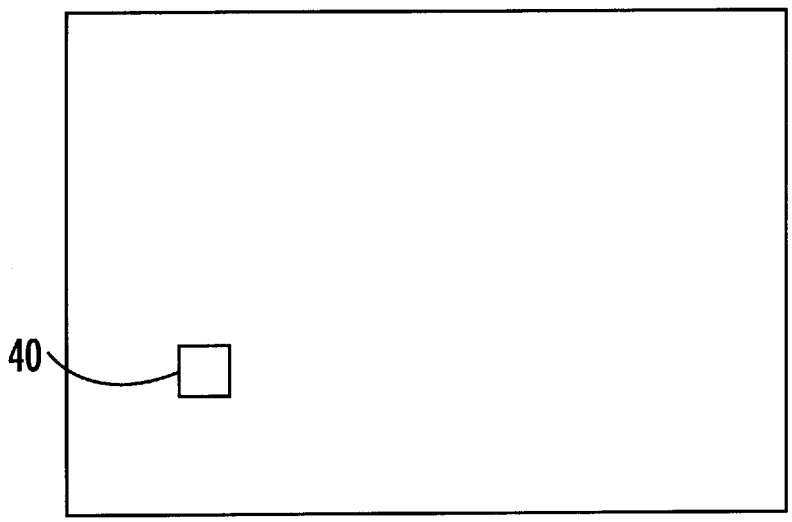
FIG. 5 is color image 4 of 4 of an illustrative display generated by the color image processing system after detecting a foreign object by its color.

In FIG. 3, the area of interest 31 of the video digital image 30 generated by the camera has been changed by the addition of a layer of material 35, a nonproblematic foreign object 37 outside of the area of interest 31, and a problematic foreign object 39 within the area of interest 31. As described below, the video detection and alert system includes a color image processing system for processing the video digital images generated by the camera. In this regard, the color video processing system initially subtracts or removes that portion of the video digital image 30 which is either outside of the area of interest 31 or is inside the area of interest, but is otherwise predetermined to not be of interest, thereby creating the video digital image shown in FIG. 4, for example. In this instance, the video processing system removes those areas between the outer boundary of the video digital image 30 and area of interest 31 as well as an inner area defined by the cutout guide 34 which becomes a featureless portion 38. Note that the nonproblematic foreign object 37 is removed from further consideration since it lies outside of the area of interest. Some objects such as the glare 32 that should be ignored are only partially excluded at this point.

Once those portions of the video digital image 30 which are either outside of the area of interest 31 or are inside the area of interest, but are otherwise predetermined to not be of interest, have been removed, the video signal processing system 47 identifies all objects having one or more predefined colors. Typically, the predefined colors have been identified in advance by the operator or the system designer to include the colors of the most common types of foreign objects. However, the predefined colors preferably do not include the colors of the composite plies or the work table. By identifying all objects having one of the predefined colors, the video processing system 47 will therefore, in all probability, identify all foreign objects within the area of interest 31.

Alternatively, the operator can identify those colors which should not be detected by the video processing system 47, such as the colors of the composite plies or the work table. As such, the video processing system of this embodiment will identify all objects having a color other than those specific colors identified by the operator.

Figure 8:
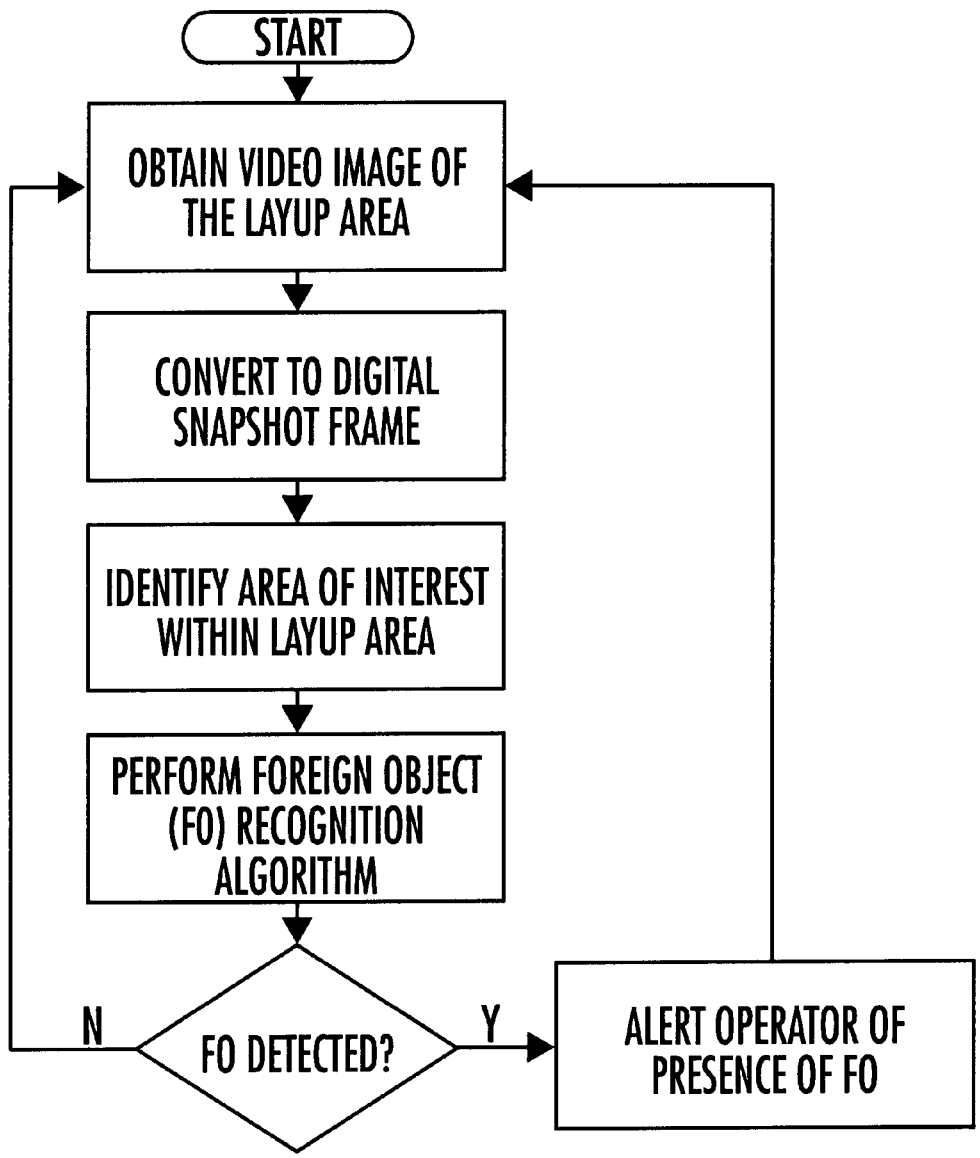
FIG. 8 is a flow diagram for the method of video detection of foreign objects.

According to either embodiment, an image of the area of interest can then be displayed to the operator. During this subsequent display to the operator, the warning system of the foreign object detection system may display the raw video digital image 30 shown in FIG. 3 with those features having an unanticipated color, such as foreign object 39, highlighted to thereby draw attention to the problematic foreign object 39. The overall foreign object detection and warning method is illustrated in FIG. 8.

Figure 9:
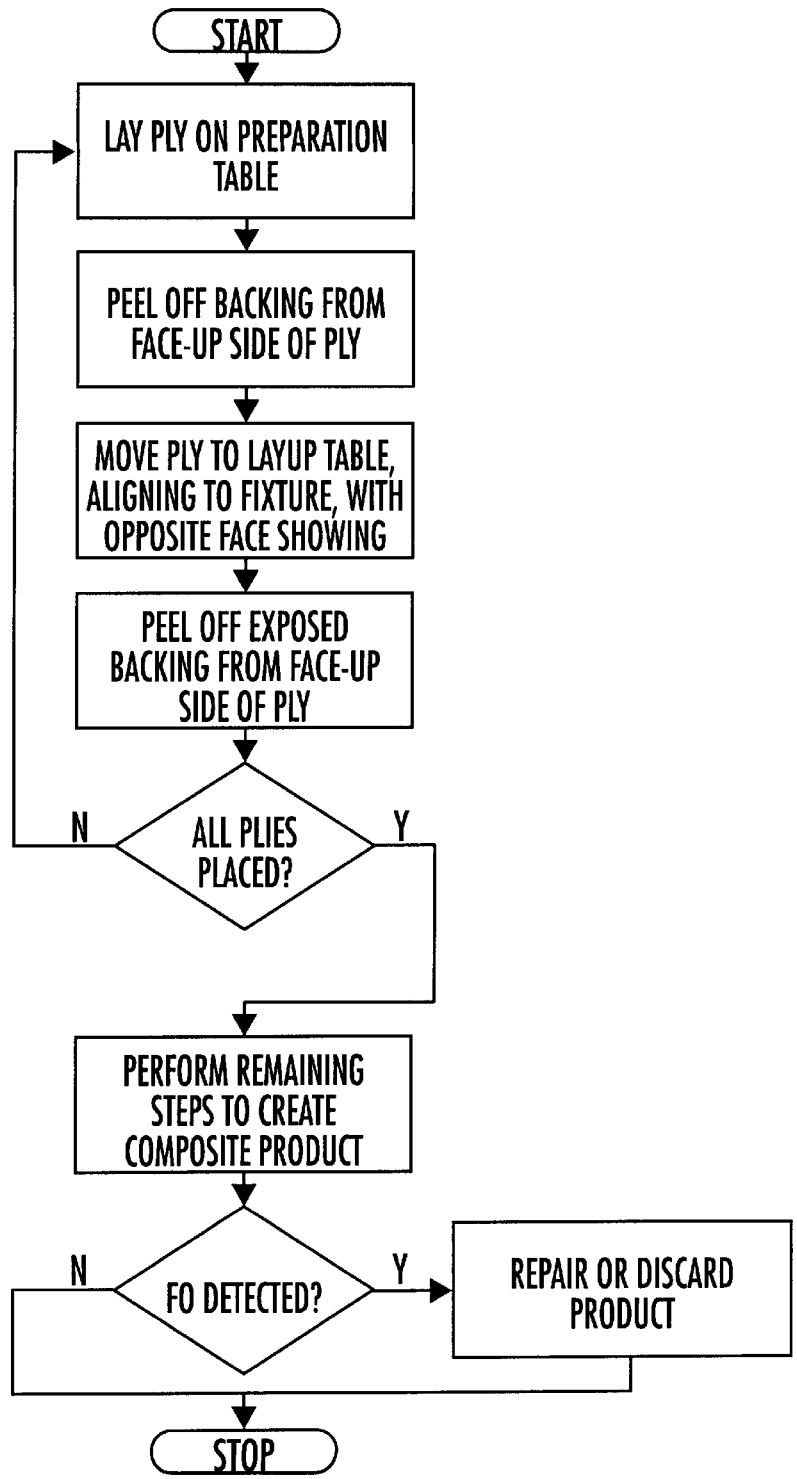
FIG. 9 is a prior art process for constructing a composite structure incorporating post-manufacturing detection of foreign objects.

As illustrated in FIG. 9, a conventional process for building the composite skin for tactical aircraft wing structures begins by laying the ply on the preparation table. Typically, two adjacent tables are used in preparing and laying up the layers of material, or composite plies. The preparation table is a typical, work table upon which a layer of composite material is laid. The protective backing is then peeled off the exposed face of the composite layer and discarded. Then, the layer of composite material is placed upon the lay-up table within the tooling or guides. The side previously exposed from which the protective backing has been removed is now laid face down upon the lay-up table. Since the protective backing has been removed from the downwardly facing side of the composite layer, the composite layer adheres to the underlying composite layer. The other side of the composite layer is now exposed and has its protective backing peeled off and discarded in preparation for another composite layer to be placed thereupon. Once the entire composite structure has been laid up and cured, the resulting composite structure is subjected to non-destructive testing to detect flaws and/or foreign objects within the otherwise completed structure. This last step of post-manufacture non-destructive testing emphasizes the reactive rather than proactive controls for foreign objects practiced by conventional composite fabrication processes.

Figure 10:
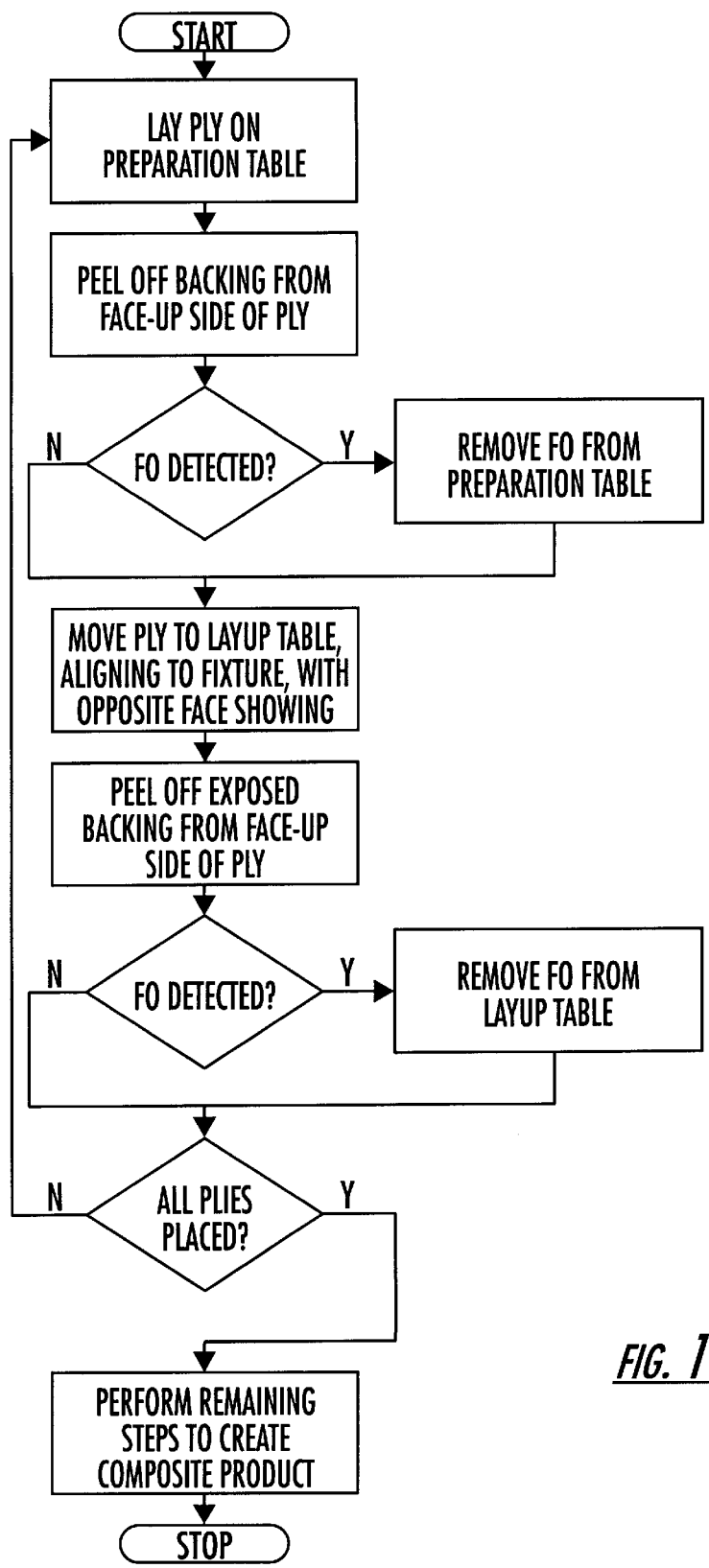
FIG. 10 is a new process for constructing a composite structure incorporating concurrent detection of foreign objects with manufacture.

As illustrated in FIG. 10, the foreign object detection and warning system and method monitors these work surfaces as the composite plies are laid up to detect foreign objects prior to completing the composite fabrication process. Although the foreign object video detection and warning system can monitor work surfaces of any size, the foreign object video detection and warning system of one embodiment continuously monitors a 5 ft by 12 ft work surface in demonstrated to detect one-quarter inch square foreign objects. It is anticipated that production versions could consistently detect one-half inch square objects. If the foreign object video detection and warning system detects a foreign object at anytime during the fabricating process, the operator is warned and can take proactive steps to remove the foreign object and rework the part, prior to completely assembling and curing the part. Conventional post-manufacture non-destructive testing can still be employed in conjunction with the video detection and warning system to detect other types of defects such as material flaws, composite curing discrepancies, or handling errors.

The present invention can advantageously be included into an existing manufacturing environment at relatively low cost. For example, the cost of one embodiment of the foreign object video detection and warning system was approximately the same as the cost of one manufactured article that would otherwise have been scrapped for including foreign objects. The cost is even lower if a general purpose computer is available at the location that can be time shared with this monitoring process or if multiple work stations can utilize the same computer.

Another advantage of the video detection and warning system is that the cameras need not be physically repositioned to account for changes in the area of concern. Instead, the color video image processing system can select the particular area of interest from the larger video image based upon input by the operator. Although some minimum level of lighting is needed as described below, the work surfaces advantageously need not be specifically illuminated to obtain appropriate color images. Since the video detection and warning system detects foreign objects based upon color, the image processing system need not be programmed with a master image to which the current image is compared, thereby simplifying the design of the video detection and warning system.

Figure 11:
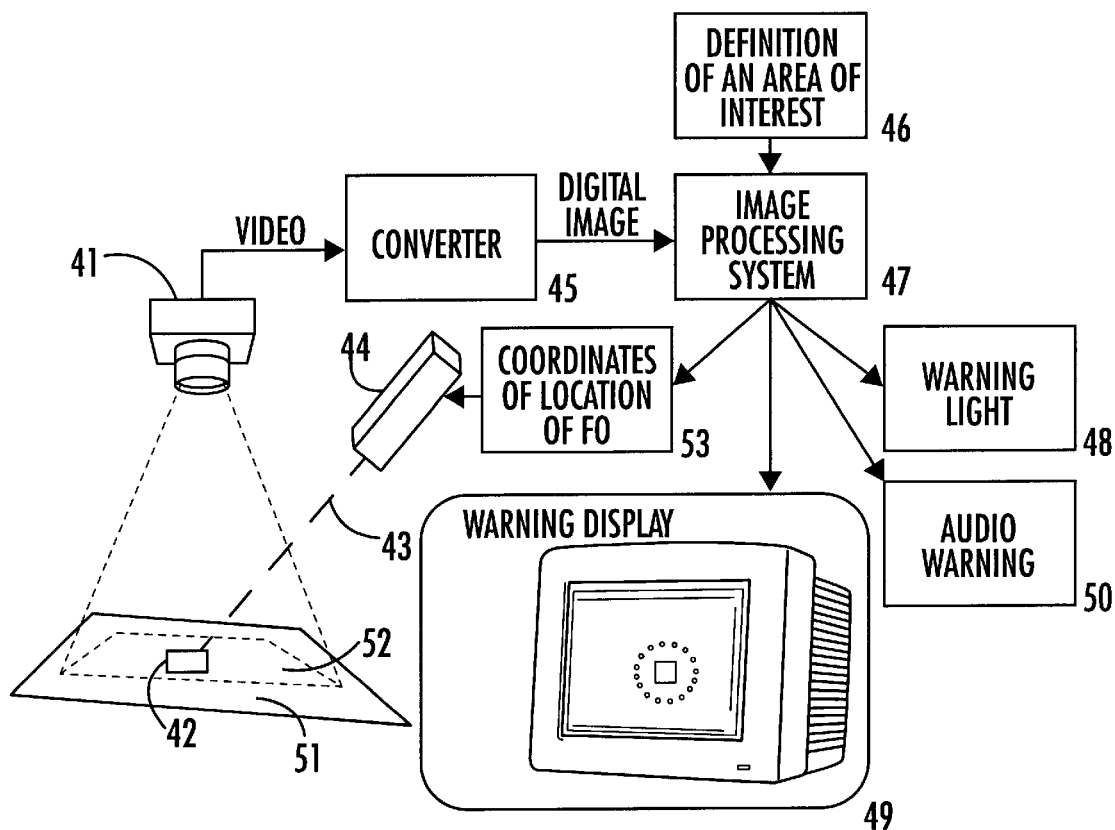
FIG. 11 is a block schematic of an embodiment of the video detection apparatus for identifying foreign objects.

As illustrated in FIG. 11, one embodiment of the foreign object video detection and warning system was demonstrated using off-the-shelf, commercial hardware with modified commercially available software. The foreign object video detection and warning system includes an NTSC video camera 41 attached to an existing frame structure shown in FIG. 1, approximately ten feet above the preparation table. The foreign object video detection and warning system also includes another video camera 41 similarly placed above the lay-up table. As an alternative to NTSC video cameras, the foreign object video detection and warning system can include digital cameras if so desired. Based upon the color and contour of the underlying table, the detection technique can be correspondingly modified. For example, a simpler color detection algorithm may be appropriate for a preparation table presenting a uniform background. However, the lay-up table has a number of guides for positioning the layers of material, or composite plies, so as to disadvantageously create varying colors, glare and a contoured work surface, thereby requiring a more sophisticated detection algorithm.

The video cameras of one advantageous embodiment capture and transmit standard television format video signals, via coaxial cable, to a converter 45, in this instance a FRAME GRABBER™ converter by Premier Electronics Card Products of the United Kingdom. The FRAME GRABBERS™ converter of this embodiment includes a Microsoft WINDOWS™ compatible PCMCIA Type II video capture card which accepts the video signals and provides a corresponding digital color image to the video image processing system. In one embodiment, the video image processing system includes an Intel PENTIUM™ microprocessor-based personal computer on which Microsoft VISUAL BASIC™ software has been installed for controlling Media Cybernetics IMAGE PRO™ software. The IMAGE PRO™ software provides color image processing capability and color channel processing capabilities in order to separate objects, including foreign objects, from background based on color and to isolate a group of colors for further processing and analysis. The IMAGE PRO™ software also provides computer display representations of the digital color image for presentation upon an associated display. The video processing system can also overlay the outline of the area of interest upon the color image presented by the display 49 and can highlight foreign objects by presenting the foreign objects in color or by otherwise designating the foreign objects, such as by superimposing a flashing red ellipse shape over the image of the foreign object on the color image display. The video image processing system and, in particular, the IMAGE PRO™ software permits the operator to select an area of interest that is subsequently shown overlaid on the digital color image of the work surface. The foreign object video detection and warning system can include other types of warning devices in addition to highlighting the detected foreign object in the color image presented upon the display device 49, such as audible warnings or warning lights which are actuated by the video image processing system. The iteration rate of the foreign object video detection and warning system preferably makes recognition and warning appear instantaneous for the operator.

The foreign object detection and warning system performs better when the lighting is optimized since places on the work surface that return a reflection from the lighting may otherwise appear as a light colored foreign object and produce a false alarm. However, compensating for such glare can reduce the sensitivity of the detection system. Thus, the lighting can be optimized by utilizing diffuse lighting, controlling the direction of the lighting, using glare reducing filters, and using spectral filters so that any reflection is not directed toward a video camera, and covering the background surface with matte black material to minimize, if not eliminate, undesirable reflections, since the texture and color of the work surface should absorb rather than reflect light. The lighting should also be sufficiently bright for the sensitivity of the chosen video camera. In addition, extraneous sources of light can be shielded by enclosing portions of the working area.

The foreign object detection and warning system also performs better At when the work surface is made as nearly homogeneous in texture and color as possible, especially if the work surface can be made to be as dissimilar from all expected forms of foreign objects as possible. In one advantageous embodiment, the preparation table was uniformly covered with a matte black paper used in the photographic industry commonly called black backdrop.

In order to increase the resolution or to obtain a larger viewing area, the foreign object video detection and warning system can include a camera designed and positioned as described below. First, the camera could be brought closer to the work surface. Second a higher resolution camera could be used. Third, a plurality of cameras could be used. Fourth, the camera position could be controllably movable. Fifth, the direction of the field of view of the camera could be controllably steered. Sixth, the camera could incorporate magnification lenses.

It is also anticipated that the removal of detected foreign objects could be expedited by integrating the foreign object video detection and warning system with an intense, narrowly-focused directional light, such as an eye-safe laser 44 with a frequency in the visual spectrum. The color image processing system 47 could provide the coordinates of the detected foreign object 42 to the laser 44 which is thereafter oriented so as to emit a laser beam directed to the coordinate at which the foreign object is located upon the work table, such as by pointing at the center of the foreign object, defining the outline of the foreign object, or illuminating the entire foreign object. The illumination of the foreign object can continue until all FO is found and removed. This technique is especially appropriate for manufacturing processes having laser pointers integrated with computer aided design or computer aided manufacturing CAD/CAM electronic design files capability.

Although the above-described embodiment of the foreign object video detection and warning system converts the television video image to a digital color image, this conversion may not be necessary with other embodiments. For examples, the video camera could directly produce a digital color image suitable for digital color image processing. Alternatively, an analog color image processing system could directly process a television format video signal.

Alternatively, the video camera could be replaced with other optical scanning means. For example, the necessary color and/or contrast information could be gathered by scanning the work table with a single point detector. The pattern of scanning could be rastered or specifically steered only over the area of interest. The detector could also be a single line scan camera.

Although the foreign object video detection and warning system of the illustrated embodiment includes an audio warning, a warning light and a video display warning the operator of the foreign object, the foreign object video detection and warning system could include a wide variety of other warning methods or devices. An alternative warning technique could include an electromagnetic signal generated by the computer. For example, the computer could contact a vibrating beeper carried by the operator.

The foreign object video detection and warning system also preferably optimizes the timing of the warning. For example, the foreign object video detection and warning system could delay the warning in order to provide the operator with the opportunity to remove a foreign object before the foreign object detection system and method assumes that the operator has overlooked the foreign object. In particular, an annoying audio warning could be delayed although other visual warnings are not delayed. This selective delay of the various types of warnings would reduce nuisance alarms that ultimately degrade the utility of the system. Also, the color image processing system could provide text based warning messages for operators likely to view a display screen. Moreover, automated systems for preparing and laying material could incorporate the foreign object video detection and warning system such that the warning signal interrupts an automated system controller, directs a robotic manipulator to remove the foreign object, or transmits a signal to a human operator, perhaps at a distance, to intercede in correcting the problem, such as by removing the foreign object, prior to continuing the manufacturing process.

Although not applicable for the types of material inspected in the above-described embodiment, the work table could be backlit, if so desired. Thin and translucent materials would thus disclose foreign objects on top or under the layer of material due to the unique color provided by the foreign object or the reduced level of light transmitted therethrough. By detecting the relative levels of light, the foreign object video detection and warning system of this embodiment could also detect foreign objects that are the same color as the layer material, such as a scrap piece of the same material.

In one advantageous embodiment, the foreign object video detection and warning system receives operator input via a personal computer keyboard, a mouse or a hand held remote control to define the area of interest on the work surface for foreign object detection. It is anticipated, however, that a computer aided design, computer aided manufacturing (CAD/CAM) system could be integrated with the manufacturing process and that the area of interest can be predefined via the CAD/CAM system. Alternatively, the physical limits of the digital color image could be constrained to be coextensive with the area of interest.

Although color image processing is described heretofore, the foreign object video detection and warning system could also distinguish foreign objects based upon gray scale image processing since most foreign objects would differ in contrast from the composite plies. This implementation would be particularly advantageous in low light situations in which a laser is used.

By utilizing the measurement capabilities of the foreign object video detection and warning system, the discrimination of foreign objects can be further enhanced. For example, the foreign object video detection and warning system of the illustrated embodiment can provide the Cartesian coordinates of the center of the object and information regarding the area of the foreign object. By detecting only those foreign objects having a size less than a predetermined value, the number of false alarms can therefore be reduced. For example, since relatively large, silver-colored tools are often used on the work surface, the system may be configured to only actuate an alarm for any foreign object equal to or larger than the size of the blade of an EXACTO knife.

By utilizing the area calculation and comparison as described above, it is anticipated that the foreign object detection system and method could be applied to other situations, such as monitoring an aircraft parking area or manufacturing shop floor for foreign objects. Those objects deemed too large to be a foreign object would be ignored. Objects too small to be hazardous could also be excluded by calculating their area, but would probably be ignored anyway due to resolution limitations on the system. If the video camera is not perpendicular to the area of interest, the foreign object video detection and warning system could still calculate the size of a foreign object by determining the range or distance from the camera to the foreign object, such as with a laser range finder, or by predefining a description of the environment. For example, a look-up table of distances from the camera to the foreign object could be predetermined for the various angles of azimuth and direction.

Furthermore, it is anticipated that the foreign object video detection and warning system could provide cueing and activation commands to an automated foreign object removal device such as a robotic pick-and-place device, vacuum chuck, or air jet.

In addition, the foreign object video detection and warning system could also incorporate a learning algorithm, such as a neural network, to assist in detecting foreign objects.

In the drawings and specification, there has been set forth a preferred embodiment of the invention, and, although specific terms are employed, the terms are used in a generic and descriptive sense only and not for purposes of limitation, the scope of the invention being set forth in the following claims.

That what is claimed:

1. A detector for finding foreign objects lying on a work surface of a composite structure and providing warning, the detector comprising:
    a light source for illuminating the work surface with diffuse light;
    a video camera having a field of view, said video camera oriented such that the work surface is in the field of view for producing a color image of the work surface;
    a color image processing system, responsive to said video camera, for analyzing a predefined area of interest within the field of view of the video camera, said color image processing system comprising means for accepting a definition of the area of interest, said color image processing system also comprising means for discriminating a foreign object within the area of interest of the color image based on visual attributes of the foreign object including differences in the color of the foreign objects and the work surface, said color image processing system further comprising means for determining a location of the foreign object on the work surface; and
    a warning mechanism, responsive to said color image processing system, for alerting an operator when a foreign object is present on the work surface of the composite structure, said warning mechanism comprising an optical pointing device for illuminating at least a portion of the foreign object.

2. A detector according to claim 1 wherein said warning mechanism comprises a display for displaying the color image provided by said video camera with the area of interest delineated and the foreign object highlighted.

3. A detector according to claim 1 wherein said warning mechanism comprises a light for illumination upon detecting a foreign object.

4. A detector according to claim 1 wherein said warning mechanism comprises an audible warning device for emitting an audio signal upon detecting a foreign object.

5. A detector according to claim 1 further comprising an optical pointing device for receiving the location of the foreign object from said color image processing system and for specifically illuminating the foreign object on the work surface.

6. A detector according to claim 1 wherein said color image processing system further comprises means for accepting a list of colors associated with foreign objects.

7. A detector according to claim 1 wherein said color image processing system discriminates the foreign object by detecting objects having a color different from the color of the background in the area of interest of the digital color image.

8. A detector according to claim 7 wherein said color image processing system further comprises means for ignoring one or more predetermined colors so as to reduce false alarms.

9. A detector according to claim 7 wherein said color image processing system further comprises means for reducing illumination glare on the work surface so as to reduce false alarms.

10. A detector according to claim 7 wherein said color image processing system reduces false alarms by further comprising means for subtracting a predefined representation of the field of view from the color image so that remaining discrepancies represent foreign objects.

11. A detector according to claim 1 wherein said color image processing system further comprises means, responsive to operator actuation, for accepting the definition of the area of interest.

12. A detector according to claim 1 wherein said color image processing system further comprises means for accepting the definition of the area of interest in the form of an electronic computer automated design file.

13. The detector of claim 1 in which said color image processing system further comprises a neural network trained to recognize foreign objects.

14. A detector according to claim 1 wherein said warning mechanism provides an electromagnetic signal.

15. A method for detecting a foreign object during manufacturing of composite structures that include one or more layers of material and for warning an operator of the detected foreign object, said process comprising the steps of:
    illuminating the work surface with diffuse light;
    obtaining a video representation of a work surface;
    transmitting the video representation as a video signal;
    converting the video signal to a digital color image;
    defining an area of interest, said defining step comprising subtracting predefined areas outside of the area of interest in which the presence of foreign objects is unimportant form the digital color image;
    detecting a foreign object within the area of interest based upon the color of the foreign object relative to the colors of one or more layers of material;
    warning the operator of the presence of the foreign object; and
    removing the foreign object before any further manufacture of the composite structure.

16. A method according to claim 15 wherein said step of warning the operator of the presence of the foreign object so that the foreign object may be removed further comprises displaying the color image and highlighting the foreign object within the displayed color image.

17. A method according to claim 15 wherein said step of subtracting predefined areas from the color image comprises the steps of:

retaining a portion of the color image that corresponds to portions of the work surface containing the one or more layers of material;

subtracting colors of the one or more layers of material from the retained portion of the color image; and designating those objects within the retained portion of the color image which remain colored as foreign objects.

18. A method according to claim 17 wherein said step of subtracting predefined areas from the color image further comprises the step of subtracting variations in the digital color image attributable to illumination glare on the work surface from the digital color image.

19. A method according to claim 15 wherein said step of warning the operator of the presence of the foreign object so that the foreign object can be removed further comprises illuminating a warning light.

20. A method according to claim 15 wherein said step of warning the operator of the presence of the foreign object so that the foreign object may be removed further comprises transmitting an audio signal.

21. The method of claim 15 in which said step of obtaining a video representation of the work surface further comprises the step of obtaining video representations of the work surface from a plurality of vantage points to increase the resolution of the resulting digital color image, thereby facilitating detection of foreign objects while permitting additional contour variations in the work surface.

22. A detector for finding foreign objects laying on a work surface of a composites structure and providing warning, the detector comprising:

a light source for illuminating the work surface with diffuse light;

a video camera having a field of view, said video camera oriented such that the work surface is in the field of view for producing a video signal thereof;

a converter, responsive to said video camera, for iteratively transforming the video signal to a digital color image;

a video signal carrier extending between said video camera and said converter for transferring the video signal to the converter;

a color image processing system, responsive to said video camera, for analyzing a predefined area of interest within the field of view of the video camera, said color image processing system comprising means for discriminating a foreign object within the area of interest of the color image based on visual attributes of the foreign object including differences in the color of the foreign objects and the work surface, said color image processing system further comprising means for determining a location of the foreign object on the work surface; and a warning mechanism, responsive to said color image processing system, for alerting an operator when a foreign object is present on the work surface of the composite structure; said warning mechanism comprising an optical pointing device for illuminating at least a portion of the foreign object.

* * * * *

UNITED STATES PATENT AND TRADEMARK OFFICE
CERTIFICATE OF CORRECTION

PATENT NO. : 6,064,429
DATED : May 16, 2000
INVENTOR(S) : Belk et al.

It is certified that error appears in the above-identified patent and that said Letters Patent is hereby corrected as shown below:

Title page, [56] References Cited, U.S. PATENT DOCUMENTS, line 11, "Grezee et al." should read --Crezee et al.--; line 13, "Laitinen" should read --Laitinen et al.--; line 15, "Heida et al." should read --Hieda et al.--; line 19, "Sogabe" should read --Sogabe et al.--.

Title page, [56] References Cited, U.S. PATENT DOCUMENTS, insert the following:

| | | |
|---|---|---|
| --5,258,917 | 11/1993 | Bruder, et al. |
| 5,426,509 | 6/1995 | Peplinski |
| 4,437,115 | 3/1984 | Yoshida |
| 5,452,370 | 9/1995 | Nagata |
| 5,331,312 | 7/1994 | Kudoh |
| 5,486,819 | 1/1996 | Horie--. |

Signed and Sealed this

First Day of May, 2001

Attest:

NICHOLAS P. GODICI

*Attesting Officer*     *Acting Director of the United States Patent and Trademark Office*